(12) United States Patent
Montia et al.

(10) Patent No.: US 11,690,937 B2
(45) Date of Patent: Jul. 4, 2023

(54) ANTIMICROBIAL COMPOSITIONS COMPRISING MINOCYCLINE AND DEGRADATION PRODUCTS OF OXIDIZED CELLULOSE

(71) Applicants: Omrix Biopharmaceuticals Ltd., Rehovot (IL); Ethicon, Inc., Somerville, NJ (US)

(72) Inventors: Eve Montia, Rehovot (IL); Dwayne Looney, Flemington, NJ (US); Theresa Scheuble, Rockaway, NJ (US); Ronen Eavri, Binyamina (IL); Roi Mashiach, Kiryat-Ono (IL)

(73) Assignees: Omrix Biopharmaceuticals Ltd., Rehovot (IL); Ethicon, Inc., Sommerville, NJ (US)

( * ) Notice: Subject to any disclaimer, the term of this patent is extended or adjusted under 35 U.S.C. 154(b) by 8 days.

(21) Appl. No.: 17/345,728

(22) Filed: Jun. 11, 2021

(65) Prior Publication Data
US 2021/0316048 A1 Oct. 14, 2021

Related U.S. Application Data

(62) Division of application No. 16/195,909, filed on Nov. 20, 2018, now Pat. No. 11,045,588.

(60) Provisional application No. 62/598,684, filed on Dec. 14, 2017.

(30) Foreign Application Priority Data

Dec. 14, 2017 (IL) .......................................... 256325

(51) Int. Cl.
| | |
|---|---|
| *A61L 31/16* | (2006.01) |
| *A61P 31/04* | (2006.01) |
| *A01N 1/00* | (2006.01) |
| *A61L 27/54* | (2006.01) |
| *C12N 5/00* | (2006.01) |
| *A61L 27/20* | (2006.01) |
| *A61K 31/717* | (2006.01) |
| *A61K 31/65* | (2006.01) |
| *A61L 15/28* | (2006.01) |
| *A61L 15/44* | (2006.01) |
| *A61L 26/00* | (2006.01) |

(52) U.S. Cl.
CPC .............. *A61L 31/16* (2013.01); *A01N 1/00* (2013.01); *A61K 31/65* (2013.01); *A61K 31/717* (2013.01); *A61L 15/28* (2013.01); *A61L 15/44* (2013.01); *A61L 26/0023* (2013.01); *A61L 27/20* (2013.01); *A61L 27/54* (2013.01); *A61P 31/04* (2018.01); *C12N 5/0018* (2013.01); *A61L 26/0066* (2013.01); *A61L 2300/404* (2013.01); *A61L 2300/406* (2013.01)

(58) Field of Classification Search
CPC .......... A61L 31/16; A61L 15/28; A61L 15/44; A61L 26/0023; A61L 27/20; A61L 27/54; A61L 26/0066; A61L 2300/404; A61L 2300/406; A61P 31/04; A01N 1/00; A61K 31/65; A61K 31/717; C12N 5/0018
See application file for complete search history.

(56) References Cited

U.S. PATENT DOCUMENTS

| | | | |
|---|---|---|---|
| 5,670,542 A | 9/1997 | Yu | |
| 7,919,480 B2 | 4/2011 | Liu et al. | |
| 8,646,456 B2 | 2/2014 | Touati | |
| 9,533,069 B2 | 1/2017 | Larsen | |
| 9,585,988 B2 * | 3/2017 | McJames | A61L 31/16 |
| 9,675,728 B2 * | 6/2017 | Cullen | A61L 15/44 |
| 10,086,115 B2 | 10/2018 | Mcjames, II et al. | |
| 2003/0133967 A1 | 7/2003 | Ruszczak et al. | |
| 2006/0172000 A1 | 8/2006 | Cullen et al. | |
| 2008/0275230 A1 | 11/2008 | Liu | |
| 2009/0246287 A1 * | 10/2009 | Shoseyov | A61K 31/716 424/45 |
| 2011/0059177 A1 | 3/2011 | Thatte | |
| 2011/0123517 A1 | 5/2011 | Gallagher | |
| 2014/0031912 A1 | 1/2014 | Mcjames et al. | |
| 2016/0030476 A1 | 2/2016 | Vachon et al. | |
| 2017/0319754 A1 * | 11/2017 | Pulapura | A61K 31/722 |
| 2019/0314560 A1 * | 10/2019 | Soskin | A61L 31/10 |

FOREIGN PATENT DOCUMENTS

EP 1263485 A1 12/2002

OTHER PUBLICATIONS

Bajpai, et al., Minocycline-loaded cellulos nano whiskers/poly(sodium acrylate) composite hydrogel films as wound dressing, Int J. Bio. Macro, 2015, pp. 76-85, vol. 79.
Clement L.K. Chia et al., "The Use of Collatamp G, Local Gentamicin-Collagen Sponge, in Reducing Wound Infection", Int. Surg. 2014 (99).
International Search Report & Written Opinion dated Jun. 20, 2019 for App No. PCT/IL2018/000010 pp. 10.
Jarmila Vytrasova et al: "Antimicrobial effect of oxidized cellulose salts", Journal of Industrial Microbiology & Biotechnology ; Official Journal of the Society for Industrial Microbiology, Springer, Berlin, DE, vol. 35, No. 11, Aug. 20, 2008 (Aug. 20, 2008), pp. 1247-1252, XP019637516, ISSN: 1476-5535, DOI: 10.1007/S10295-008-0421-Y.

(Continued)

*Primary Examiner* — Robert A Wax
*Assistant Examiner* — Olga V. Tcherkasskaya
(74) *Attorney, Agent, or Firm* — David R. Crichton

(57) ABSTRACT

Provided is an antimicrobial composition comprised of at least one degradation product of oxidized cellulose (OC), such as oxidized regenerate cellulose (ORC), and minocycline, methods of preparation thereof and uses thereof.

5 Claims, 6 Drawing Sheets

(56) References Cited

OTHER PUBLICATIONS

Martina, et al., Oxycellulose:Significant Characteristics in Relation to Its Pharmaceutical and Medical Applications, Advances in Polymer Technology, 2009, pp. 199-208, vol. 28 Issue 3.
Schmitz, et al., Minocycline Protects Oligodendroglial Precursor Cells Against Injury Caused by Oxygen-Glucose Deprivation, Journal of Neuroscience Research, Jan. 18, 2012, pp. 933-944, vol. 90.

* cited by examiner

ANTIMICROBIAL COMPOSITIONS COMPRISING MINOCYCLINE AND DEGRADATION PRODUCTS OF OXIDIZED CELLULOSE

CROSS-REFERENCE TO RELATED APPLICATION

This application is a divisional application of co-pending U.S. application Ser. No. 16/195,909 filed on Nov. 20, 2018, which claims priority to U.S. Provisional Application No. 62/598,684 filed on Dec. 14, 2017 and Israeli Application No 256325 filed on Dec. 14, 2017, the complete disclosure of which is hereby incorporated herein by reference for all purposes.

FIELD OF THE INVENTION

The invention relates, inter alia, to the field of pharmaceuticals, and more specifically, but not exclusively, to an antimicrobial composition comprising at least one degradation product of oxidized cellulose (OC) (such as at least one degradation product of oxidized regenerated cellulose (ORC)) and minocycline, methods of preparation thereof and uses thereof.

BACKGROUND OF THE INVENTION

Healthcare Associated Infections (HAIs) are infections which occur during treatment for medical or surgical conditions, and may be caused by surgical procedures or devices used in medical procedures, such as catheters or ventilators.

HAI are becoming a global epidemic, resulting in significant levels of morbidity and mortality, and involving significant health care costs. Health service providers, as well as bodies responsible for payment of associated costs, are focusing on reducing HAIs to improve outcomes and control costs.

Common types of HAIs include catheter-associated urinary tract infections, surgical site infections, bloodstream infections, pneumonia and *Clostridium difficile* infections.

Surgical Site Infections (SSI) are a class of HAI which develop following surgery. Types of SSI include superficial incisional SSI, which occurs in the area of the skin where the incision was made; deep incisional SSI, which occurs beneath the incision area in muscle and the tissue surrounding the muscles; and organ or space SSI, which can occur in any area of the body other than skin, muscle and surrounding tissue that was involved in the surgery, including a body organ or a space between organs.

SSIs are currently treated with systemic antibiotics, requiring high dosage levels, from which only a small percentage of the active substance reaches the target site. However, antimicrobial resistance among the pathogens causing the infection is becoming increasingly problematic, thereby limiting the usefulness of such antibiotics in the treatment or prevention of SSIs.

Known antibiotic products include Medtronic Antibacterial Envelopes sold under the trademark TYRX™, comprising a combination of minocycline and rifampin, which have been shown to reduce infection associated with medical devices in multiple, randomized, controlled trials; the Codman® Bactiseal® catheter for drainage of external cerebrospinal fluid, which is impregnated with rifampin and clindamycin for reduction of Gram-positive bacteria on surfaces of the catheter tube; Ethicon plus sutures, a range of triclosan-coated sutures including a product sold under the trademark named MONOCRYL® Plus Antibacterial (poliglecaprone 25) Sutures and Plus Antibacterial (polydioxanone) Sutures sold under the trademark named PDS® Sutures; and CollatampG/Septocoll E-Innocoll/Biomet, a gentamicin-soaked Collagen Sponge Dual having a dual principle of action for hemostasis and antibiotic protection.

Examples of background art include U.S. Publication No. 2014/0031912; In. Surg 2014 (99): 565-570; EP 1263485B1; U.S. Pat. Nos. 9,533,069; 8,646,456; Int. J Biol. Macro. 79 (2015): 76-85; and U.S. Publication No. 2016/0030476.

SUMMARY OF THE INVENTION

The invention, in some embodiments thereof, relates to a composition comprising minocycline and at least one degradation product (DP) of an oxidized cellulose, methods of preparation thereof and uses thereof. In some embodiments, the oxidized cellulose is oxidized regenerated cellulose (ORC).

The present inventors have surprisingly found a synergistic effect between minocycline and at least one degradation product of ORC, such that significantly lower levels of minocycline than are generally known in the art when using minocycline alone can be used to obtain effective antimicrobial activity.

Specifically, in the composition of the present invention, minocycline may be present at a concentration of from about 0.0126 μg/ml. This is significantly lower than the concentrations in the range of 0.06-0.5 μg minocycline per ml minimum inhibitory concentration (referred to as "MIC") values for *S. aureus* according to CLSI, see Table 1) which are known in the art, thereby resulting in less development of antibiotic resistance and fewer side effects, while providing broad spectrum antibiotic activity.

The composition, in some embodiments thereof, is suitable for local administration to subjects suffering from or at risk of an SSI, providing a higher level of antimicrobial activity than that of currently known compositions, such that lower amounts of antibiotics than are presently known in the art can be used.

As used herein, the terms "degradation product of OC" or "degradation products of OC" relate to one or more materials obtained upon degradation of OC, in an aqueous solution such as aqueous biological fluid such as serum, blood, plasma and the like or in non-biological solution such as PBS. As used herein, the terms "degradation product of ORC", or "degradation products of ORC" relate to one or more materials obtained upon degradation of ORC, in an aqueous biological fluid, such as serum, blood, plasma and the like or in non-biological fluid such as a solution of PBS.

Degradation products of OC (such as degradation products of ORC) may include side products present during the production of OC (such as production of ORC). Degradation products may include products obtained upon further oxidation. Degradants can comprise 2-keton ORC degradants, 3-keton ORC degradants 2,3 dial dolly de cellulose degradants, 2,3-dicarboxyl cellulose degradants, and combinations thereof.

As used herein, the term "antimicrobial" is intended to include destroying or inhibiting the growth of microorganisms such as pathogenic bacteria.

The term "antibiotic" as used herein relates to a substance such as a chemical that can destroy harmful bacteria or limit their growth. The substance can be a naturally produced or a synthetic material. In some embodiments, substance can be produced by a microorganism, or can be a semisynthetic substance derived from a microorganism.

As used herein, the term "minocycline" relates to a long-acting, broad-spectrum, antibiotic drug. $C_{23}N_{27}N_3O_7$, of CAS No, 10118-90-8, derived from tetracycline, or a pharmaceutically acceptable salt thereof. In some embodiments, minocycline is administered in the form of its hydrochloride $C_{23}H_{27}N_3O_7 \cdot HCl$ of CAS No. 13614-98-7.

The term "minocycline" as used herein, is intended to include, but not limited to, minocycline and pharmaceutically acceptable salt thereof, pharmacologically active derivatives of minocycline, including both individual enantiomers of minocycline (dextrogyral and levogyral enantiomers) in their substantially pure form and their pharmaceutically acceptable salts, mixtures (in any ratio) of minocycline enantiomers and their pharmaceutically acceptable salts, and active metabolites of minocycline and their pharmaceutically acceptable salts.

The term "pharmaceutically acceptable salts" as used herein, includes salts which are suitable for use in contact with the tissues of humans without undue toxicity, irritation, allergic response and the like, which are well known in the art. Examples of pharmaceutically acceptable salts include, but are not limited to, any of the salts or co-crystals of minocycline selected from hydrochloride, hydrobromide, sulphate, citrate, phosphate, maleate, formate, acetate, nitrate, mesylate, succinate, benzoate and the like. The salts may be in the form of solvate, hydrate, hemihydrates, or anhydrous forms.

As used herein, the term "rifampin" relates to a naturally-occurring antibiotic, $C_{43}H_{58}N_4O_{12}$, of CAS No. 13292-46-1, produced by the soil bacterium *Amycolatopsis rifamycinica*, or a pharmaceutically acceptable salt thereof.

As used herein, the term "clindamycin", relates to a semi-synthetic antibiotic, $C_{18}H_{33}ClN_2O_5S$, of CAS No. 18323-44-9, derived from lincomycin, a natural antibiotic produced by the actinobacterium *Streptomyces lincolnensis*, or a pharmaceutically acceptable salt thereof. In some embodiments, clindamycin is administered in the form of its phosphate, $C_{18}H_{34}ClN_2O_8PS$, of CAS No. 24729-96-2 or hydrochloride, $C_{18}H_{34}Cl_2N_2O_5S$ of CAS No. 21462-39-5 or Hydrochloride Monohydrate of CAS Number 58207-19-5.

Aspects and embodiments of the invention are described in the specification hereinbelow and in the appended claims.

According to an aspect of some embodiments described herein, there is provided an antimicrobial composition comprising at least one degradation product of oxidized cellulose (OC), and an antibiotic being minocycline.

According to some embodiments, the OC comprises oxidized regenerated cellulose (ORC).

According to some embodiments, the antimicrobial composition is devoid of an additional antibiotic.

According to some embodiments, minocycline is present in the antimicrobial composition, together with the at least one OC degradation product, at a concentration of from about 12.5 ng/ml, such as from about 12.6 ng/ml, about 13.0 ng/ml, about 13.5 ng/ml, about 14.0 ng/ml, about 14.5 ng/mi, about 15.0 ng/ml, about 15.5 ng/axil, about 16.0 ng/ml, about 16.5 ng/ml, about 17.0 ng/ml, about 17.5 ng/ml, about 18.0 ng/ml, about 18.5 ng/ml, about 19.0 ng/ml, about 19.5 ng/ml, about 20.0 ng/ml, about 20.5 ng/ml, about 21.0 ng/ml, about 21.5 ng/ml, about 22.0 ng/ml, about 22.5 ng/ml, about 23.0 ng/ml, about 23.5 ng/ml, about 24.0 ng/ml, about 24.5 ng/ml, or about 25.0 ng/ml, including any value and range therebetween.

According to some embodiments, minocycline is present in the antimicrobial composition, together with the at least one OC degradation product, at a concentration of at least about 12.6 ng/ml.

According to some embodiments, minocycline is present in the antimicrobial composition, together with the at least degradation product of OC, at a concentration of up to about 25 ng/ml, such as up to about 12.6 ng/ml, about 13.0 ng/ml, about 13.5 ng/ml, about 14.0 ng/ml, about 14.5 ng/ml, about 15.0 about 15.5 about 16.0 ng/ml, about 16.5 ng/aril, about 17.0 ng/ml, about 17.5 ng/ml, about 18.0 ng/ml, about 18.5 ng/ml, about 19.0 ng/ml, about 19.5 ng/ml, about 20.0 ng/ml, about 20.5 about 21.0 ng/ml, about 21.5 ng/ml, about 22.0 ng/ml, about 22.5 ng/ml, about 23.0 ng/ml, about 23.5 ng/ml, about 24.0 ng/ml, about 24.5 ng/ml, or about 25.0 ng/axil, including any value and range therebetween.

According to some embodiments, minocycline is present in the antimicrobial composition at a concentration which is from about 2 to about 20 times lower than the MIC achieved in the absence of at least one degradation product of OC, i.e. minocycline is from about 2 times to about 20 times more effective in the presence of the degradation product of OC, for example, about 2 times, about 3 times, about 4 times, about 5 times, about 6 times, about 7 times, about 8 times, about 9 times, about 10 times, about 11 times, about 12 times, about 13 times, about 14 times, about 15 times, about 16 times, about 17 times, about 18 times, about 19 times or about 20 times more effective.

MIC relates herein to the lowest concentration of a chemical which prevents bacterial growth in a solution when the growth is monitored at an OD range of 595-600 nm e.g. as described in the "Examples" section. A MIC depends on the microorganism, the affected human being (in vivo only), and the antibiotic.

For example, the MIC of a chemical is determined by preparing solutions of the chemical in vitro at increasing concentrations, incubating the solutions with the separate batches of cultured bacteria, and monitoring the bacterial growth throughout time at the OD range of 595-600 nm. In order to define the MIC of a certain chemical the Effective Time 50 (ET50) is determined i.e. the time, in minutes, required for the antibiotic to induce a response halfway between the baseline and maximum OD reading at the range of 595-600 nm. The maximum OD is determined by bacterial growth in MHBII without the chemical. The first chemical concentration where the ET50 reached about ≥1650 minutes was determined as the MIC.

It has further been found that the synergistic effect of at least one degradation product of an OC and minocycline is not reduced upon addition of an additional antibiotic such as rifampin, clindamycin, or a mixture thereof, and in fact, the antimicrobial effect which occurs upon inclusion of such additional antibiotics in the compound was found to increase.

In some embodiments, the OC comprises ORC. Hence, according to some embodiments, the antimicrobial composition further comprises at least one additional antibiotic, such as, for example, rifampin, clindamycin or a combination thereof.

In some embodiments, the antimicrobial composition comprises at least one degradation product of ORC, minocycline and rifampin. In some embodiments, the antimicrobial composition comprises at least one degradation product of ORC, minocycline and clindamycin. In some embodiments, the antimicrobial composition comprises at least one degradation product of ORC, minocycline, rifampin and clindamycin.

According to some embodiments, the antibiotic composition comprises at least one additional antibiotic.

According to some embodiments, the antibiotic composition comprises at least one additional antibiotic selected from the group consisting of: rifampin, clindamycin, and a combination thereof.

According to some embodiments, minocycline is present in the antimicrobial composition, together with the at least one OC degradation product, wherein the minocycline is present at a concentration of at least about 1.26 ng/ml.

According to some embodiments the antibiotic composition comprises at least one additional antibiotic, and minocycline is present in the composition at a concentration of from about 1.26 ng/ml to about 6.5 ng/ml, such as about 1.25 ng/ml, about 1.5 ng/ml, about 1.75 ng/ml, about 2.0 ng/ml, about 2.25 ng/ml, about 2.5 ng/ml, about 2.75 ng/ml, about 3.0 ng/ml, about 3.25 ng/ml, about 3.5 about 3.75 ng/ml, about 4.0 ng/ml, about 4.25 ng/ml, about 4.5 ng/n, about 4.75 ng/ml, about 5.0 ng/ml, about 5.25 ng/ml, about 5.5 ng/ml, about 5.75 ng/ml, about 6.0 ng/ml, about 6.25 ng/ml, about 6.3 ng/ml or from about 6.5 ng/ml.

According to some embodiments, minocycline is present in the antimicrobial composition at a concentration which is from about 2 to about 200 times lower than that MIC achieved in the absence of at least one degradation product of OC and at least one additional antibiotic, i.e. minocycline is from about 2 times to about 20 times more effective in the presence of the degradation product of OC and the additional antibiotic, for example, about 2 times, about 5 times, about 10 times, about 20 times, about 30 times, about 40 times, about 50 times, about 60 times, about 70 times, about 80 times, about 90 times, about 100 times, about 110 times, about 120 times, about 130 times, about 140 times, about 150 times, about 160 times, about 170 times, about 180 times, about 190 times, or about 200 times more effective, including any value and range therebetween.

In some embodiments, rifampin is present in the antimicrobial composition at a concentration of about 70 ng/mi to about 370 ng-'ml, such as, for example, about 73.29 ng/ml about 80 ng/ml, about 100 ng/an, about 120 ng/ml, about 140 ng/ml, about 147 ng/ml, about 160 ng/ml, about 180 ng/ml, about 200 ng/ml, about 220 ng/ml, about 240 ng/ml, about 260 ng/ml, about 280 ng/ml, about 293 ng/ml, about 300 ng/ml, about 320 ng/ail, about 340 ng/ail, about 360 ng/ml or about 366 ng/'ml, including any value and range therebetween.

In some embodiments, clindamycin is present in the composition at a concentration of about 1.5 ng/ml to about 9.0 ng/ml, such as, for example, about 1.49 ng/ml, about 2.5 ng/ail, about 3.0 ng/ml, about 3.5 ng/ml, about 4.0 ng/ml, about 4.5 ng/ml, about 5.0 ng/ml, about 5.5 ng/ml, about 6.0 ng/ml, about 6.5 ng/ml, about 7.0 ng/ml, about 7.5 ng/ml, about 8.0 ng/ml, about 8.5 ng/ml or about 9.0 ng/ml, including any value and range therebetween.

According to some embodiments, the composition further comprises an acid, such as Trifluoroacetic acid (TFA).

ORC is a heterogeneous polymer, comprising both glucuronic acid and glucose units.

According to some embodiments, the at least one degradation product of ORC is selected from the group consisting of a monosaccharide and an oligosaccharide or their combination. In some such embodiments, the at least one degradation product of ORC comprises at least one monosaccharide other than glucose or an oligosaccharide.

In one embodiment, the oligosaccharide comprises a glycosiduronate. As used herein, the term "glycosiduronate" relates to any substance in which glucuronic acid is linked to another substance e.g. via a glycoside bond. For example, glucuronic acid can be linked to another glucuronic acid e.g. via a glycoside bond and/or glucuronic acid can be linked to glucose e.g. via a glycoside bond.

In some such embodiments, the monosaccharide other glucose comprises glucuronic acid.

In some embodiments, less than 10% (e.g. 9%) glucuronic acid is in a monomeric form as can be evaluated by high-performance liquid chromatography using triple pulse amperometry (as described by Dimitrijevich et al. "Degradation of Oxidized, Regenerated Cellulose" Carbohydrate Research, 198 (1990) 331-341) incorporated herein by reference. In some embodiments, oligo-glycosiduronate arising from degradation process of OC (such as ORC) comprises more than 10% (e.g. 69%) in dimeric form and up 10 moieties. In some embodiments, oligo-glycosiduronate arising from degradation process of OC (such as ORC) comprise more than 3% (e.g. 22%) having more than 10 moieties.

According to some embodiments, the composition is provided in a solid form. In some such embodiments, the solid form is selected from the group consisting of a powder (compressed or non-compressed), a granule, and the like. In some such embodiments, the composition may be packaged for use in a solid form for application to a treatment site.

According to some embodiments, the composition is provided in a liquid form, such as a solution, suspension, emulsion or the like.

Bleeding is one of the risk factors contributing to increased. SSI rate. To control blood loss at the surgical site, surgeons may use topical hemostats, such as ORC. In some embodiments of the present invention, the at least one degradation product of ORC is provided by impregnating an ORC pad with minocycline and optionally one or more additional antibiotics, and contacting the minocycline-impregnated ORC pad, with an aqueous solution, wherein degradation of the ORC occurs, thereby producing at least one degradation product of ORC, with release of the one or more antibiotics that were impregnated in the ORC pad.

According to a further aspect of some embodiments described herein, there is provided a method for the treatment of an infection in a subject in need thereof, the method comprising administering to the subject an antimicrobial composition comprising at least one degradation product of an oxidized cellulose (OC) and an antibiotic being minocycline.

According to some embodiments of the method, the infection is a surgical site infection (SSI).

In some embodiments of the method, the OC comprises oxidized regenerated cellulose (ORC).

As used herein, the term "infection" relates to the invasion and multiplication of disease-causing microorganisms, such as bacteria. An infection may cause no symptoms and be subclinical, or it may cause symptoms and be clinically apparent. An infection may remain localized, or it may spread through the blood or lymphatic vessels to become systemic (body wide). Microorganisms that live naturally in the body without resulting in disease are not considered infections. For example, certain bacteria that normally live within the mouth and intestine are not infections.

As used herein, the term "treatment" of an infection is intended to include curing, ameliorating, stabilizing or preventing the infection and/or symptoms thereof in a subject suffering from or at risk of the infection.

As used herein, the term "ameliorating" an infection includes reducing the severity and/or duration of the infection and/or symptoms thereof.

In some embodiments of the method, the treatment comprises preventing and/or ameliorating the infection and/or symptoms thereof.

In some embodiments of the method, the antimicrobial composition comprises at least one degradation product of ORC and minocycline, and is devoid of an additional antibiotic.

According to some embodiments of the method, minocycline is present in the antimicrobial composition at a concentration of from about 12.6 ng/ml.

According to some embodiments of the method, minocycline is present in the antimicrobial composition at a concentration of from about 12.6 ng/ml, such as from about 12.5 ng/ml, about 13.0 ng/ml, about 13.5 ng/ml, about 14.0 ng/ml, about 14.5 ng/ml, about 15.0 ng/ml, about 1.5.5 ng/ml, about 16.0 ng/ml, about 16.5 ng/ml, about 17.0 ng/ml, about 17.5 ng/ml, about 18.0 ng/ml, about 18.5 ng/ml, about 19.0 ng/ml, about 19.5 ng/ml, about 20.0 ng/ail, about 20.5 ng/ml, about 21.0 ng/ail, about 21.5 ng/ml, about 22.0 ng/ml, about 22.5 ng/ml, about 23.0 ng/ml, about 23.5 ng/ml, about 24.0 ng/ml, about 24.5 ng/ml, or about 25.0 ng/ml.

According to some embodiments of the method, minocycline is present in the antimicrobial composition at a concentration of up to about 25 ng/ml, such as up to about 12.6 ng/ml, about 13.0 ng/ml, about 13.5 ng/ml, about 14.0 ng/ml, about 14.5 ng/ml, about 15.0 ng/ml, about 15.5 ng/ml, about 16.0 ng/ml, about 16.5 ng/ml, about 17.0 ng/ml; about 17.5 ng/ml; about 18.0 ng/ml; about 18.5 ng/ml; about 19.0 ng/ml; about 19.5 ng/ml, about 20.0 ng/ml, about 20.5 ng/ml, about 21.0 ng/ml, about 21.5 ng/ml, about 22.0 ng/ml, about 22.5 ng/ml, about 23.0 ng/ml, about 23.5 ng/ml, about 24.0 ng/ml, about 24.5 ng/ml, or about 25.0 ng/ml.

According to some embodiments of the method, the antimicrobial composition further comprises at least one additional antibiotic. According to some such embodiments of the method, the at least one additional antibiotic is selected from the group consisting of rifampin, clindamycin, and a combination thereof.

Anti-bacterial antibiotics include, but are not limited to, aminoglycosides, carbacephems, carbapenems, cephalosporins, cephamycins, penicillins, glycopeptides, quinolones, monobactams, macrolides, fluoroquinolones, and tetracyclines.

Examples of antibiotics include, but are not limited to, Ampicillin; Amoxicillin; Aztreonam; Aziocillin; Azithromycin; Amikacin; Cephalothin; Cefaclor; Cefoxitin; Cefuroxime; Cefonicid; Cefinetazole; Cefotetan; Cefprozil; Cinoxacin; Cefetamet; Chloramphenicol; Clindamycin; Cefoperazone; Cefotaxime; Cloxacillin; Carbenicillin; Ciprofloxacin; Ceftizoxime; Ceftriaxone; Ceftazidime; Cefepime; Cephalexin; Cefixime; Co-amoxiciavuanate; Cefpodoxime; Cefsulodin; Clarithromycin; Dicloxacillin, Doxycycline; Erythromycin; Erythromycin estolate; Erythromycin ethyl succinate; Enoxacin; Erythromycin glucoheptonate; Erythromycin lactobionate; Erythromycin stearate; Fleroxacin; Gentamicin; Imipenem; Kanamycin; Lomefloxacin; Loracarbef; Methicillin; Nafcillin; Oxacillin; Mupirocin; Metronidazole; Mezlocillin; Nalidixic acid; Norfloxacin; Nitrofurantoin; Netilmicin; Ofloxacin; Penicillin G; Piperacillin; Rifampin; Streptomycin; Sulfamethoxazole; Tetracycline; Ticarcillin; Tobramycin; Teicoplanin; Trimethoprim; Vancomycin, Roxithromycin; combinations of Piperacillin and Tazobactam; and their various salts, acids, bases, and other derivatives. In some such embodiments of the method, the at least on; additional antibiotic is selected from the group consisting of rifampin and clindamycin and a combination thereof.

In some embodiments of the method, the antimicrobial composition comprises at least one degradation product of ORC, minocycline and rifampin. In some embodiments of the method, the antimicrobial composition comprises at least one degradation product of ORC, minocycline and clindamycin. In some embodiments of the method, the antimicrobial composition comprises at least one degradation product of ORC, minocycline, rifampin and clindamycin.

According to some embodiments of the method, wherein the antibiotic composition comprises at least one additional antibiotic, minocycline is present in the composition at a concentration of from about 1.26 ng/ml to about 6.5 ng/ml, such as about 1.25 ng/ml, about 1.5 ng/ml, about 1.75 ng/ml, about 2.0 ng/ml, about 2.25 ng/ml, about 2.5 ng/ml, about 2.75 ng/ml, about 3.0 ng/ml, about 3.25 ng/ml, about 3.5 ng/ml, about 3.75 ng/ml, about 4.0 ng/ml, about 4.25 ng/ml, about 4.5 ng/ml, about 4.75 ng/ml, about 5.0 ng/ml, about 5.25 ng/ml, about 5.5 ng/ml, about 5.75 ng/ml, about 6.0 ng/ml, about 6.25 ng/ml, about 6.3 ng/ml or about 6.5 ng/ml, including any value and range therebetween.

In some embodiments of the method, rifampin is present in the antimicrobial composition at a concentration of about 74 ng/ml to about 370 ng/ml, such as, for example, about 73.29 ng/ml, about 80 ng/ml, about 100 ng/ml, about 120 ng/ml, about 140 ng/ml, about 147 ng/ml, about 160 ng/ml, about 180 ng/ml, about 200 ng/ml, about 220 ng/ml, about 240 ng/ml, about 260 ng/ml, about 280 ng/ml, about 293 ng/ml, about 300 ng/ml, about 320 ng/ml, about 340 ng/ml, about 360 ng/ml or about 366 ng/ml, including any value and range therebetween.

In some embodiments of the method, clindamycin is present in the composition at a concentration of about 1.5 ng/ml to about 9.0 ng/ml, such as, for example, about 1.49 ng/ml, about 2.5 ng/ml, about 3.0 ng/ml, about 3.5 ng/ml, about 4.0 ng/ml, about 4.5 ng/ml, about 5.0 ng/ml, about 5.5 ng/ml, about 6.0 ng/ml, about 6.5 ng/ml, about 7.0 ng/ml, about 7.5 ng/ml, about 8.0 ng/ml, about 8.5 ng/ml or about 9.0 ng/ml, including any value and range therebetween.

According to some embodiments of the method, the composition is provided in a liquid torn, such as a solution, suspension, emulsion or the like.

According to some embodiments of the method, the composition is provided in a solid form.

According to some embodiments of the method, the composition is provided within a substrate selected from the group consisting of a cloth, a pad, and a mesh and a pad, wherein the minocycline is dispersed on and/or within the cloth, pad, or mesh.

In certain embodiments of the invention, the composition may further include a hemostatic agent, or other biological or therapeutic compounds, moieties or species, including drugs and pharmaceutical agents.

In one embodiment, the at least one degradation product of OC (such as at least one degradation product of ORC) is included within a device article and/or as a coating on a device/article; such as implant, pacemaker, drain, artificial knee, etc.

According to a further aspect of some embodiments described herein, there is provided a kit comprising at least one degradation product of an oxidized cellulose (OC) and an antibiotic being minocycline. In some embodiments, the OC comprises ORC.

In some embodiments of the kit, the antimicrobial composition comprises ORC and minocycline, and is devoid of an additional antibiotic.

In some embodiments of the kit, the antimicrobial composition comprises minocycline impregnated in the ORC.

According to a further aspect of some embodiments described herein, there is provided a method for the preparation of an antimicrobial composition, the method comprising combining at least one degradation product of an oxidized cellulose (OC) and an antibiotic being minocycline. In some such embodiment, the OC comprises ORC.

In some such embodiments, the at least one degradation product of ORC is obtained by immersion of ORC in an aqueous solution. Non-limiting examples of such solutions include: Dulbecco's Phosphate Buffered Saline (DPBS), Hank's Balanced Salt Solution (UBSS), HEPES buffer, (Pure) water, Tris Buffer, ACES buffer, and phosphate buffer. In some such embodiments, the at least one degradation product of ORC is obtained by immersion of ORC in an aqueous solution selected from the group consisting of Dulbecco's Phosphate Buffered Saline, Hank's Balanced Salt Solution, HEPES buffer, pure water, Iris Buffer, ACES buffer, and phosphate buffer.

In some such embodiments, the composition is used in cell culture growth media such as DMFM Medium, MEM Medium, RPMI Medium, F-10 Medium, F-12 Medium, F12 Medium, IMDM, Medium 199, Medium 199, Leibovitz L-15, MCDB Medium, McCoy's 5A, Williams' Medium, and CML Medium.

In some embodiments, the aqueous solution comprises Phosphate Buffered Saline (PBS). In some embodiments, the aqueous solution consists essentially of PBS.

In some embodiments of the method of preparation, the antibiotic is added to the ORC prior to immersion of the ORC in the aqueous solution. In some such embodiments of the method of preparation the antibiotic is added to the ORC prior to immersion of the ORC in the aqueous solution such that the antibiotic is impregnated or dispersed on or in the ORC.

In some embodiments of the method of preparation, the antibiotic is added to the aqueous solution subsequent to obtaining the at least one degradation product of ORC, i.e. the antibiotic is added to an aqueous solution comprising at least one degradation product of ORC.

In some embodiments, the composition is prepared by using a substrate comprising an OC (such as ORC) pad, wherein the minocycline is dispersed or impregnated on and/or within the pad, and after impregnation or dispersion the pad is contacted with an aqueous solution.

As used herein, the term "pad" relates to a piece of material used to protect a part of the body, give shape to something or clean something, and is intended to include a patch, a cloth, a mesh, a dressing, a fabric, a gauze, and the like.

As used herein, the term "patch" relates to a small piece of material that can be sewn or otherwise attached over a surface or wound.

As used herein, the term "cloth" relates to woven or felted fabric made from a fibre.

As used herein, the term "mesh" relates to a material made of a network of connected strands of flexible materials such as wire or thread.

As used herein, the term "dressing" relates to a covering for a wound.

As used herein, the term "fabric" relates to a flexible material consisting of a network of fibres produced by e.g., weaving, knitting, crocheting, knotting, felting or bonding.

As used herein, the term "gauze" relates to thin, loosely woven cloth used for dressings and swabs or to any material made of an open, mesh-like weave.

As used herein, the term "impregnate" means to saturate or infuse pores or spaces of a material, usually a solid material, with a substance, usually a liquid.

As used herein, the term "coating" relates to a covering layer applied to a surface of an object (usually referred to as a substrate), or to the process of applying such a covering layer.

As used herein, the term substrate relates to a material, such as a carrier, which provides the surface on which something is deposited.

As used herein, the term "solid" is intended to mean firm or stable in shape i.e. not liquid or fluid.

According to a further aspect of some embodiments described herein, there is provided an antimicrobial composition prepared as described herein.

According to a further aspect of some embodiments described herein, there is provided a cell culture growth medium comprising an antimicrobial composition as described herein.

As used herein, the term "cell growth culture medium" refers to a solid, liquid or semi-solid composition designed to support the growth of cells.

BRIEF DESCRIPTION OF THE DRAWINGS

Some embodiments of the invention are described herein with reference to the accompanying figures. The description, together with the figures, makes apparent to a person having ordinary skill in the art how some embodiments of the invention may be practiced.

In the Figures:

In FIGS. 1-6: The x-axis refers to time (min), and the y-axis refers to optical density (OD) at 600 nm.

FIG. 2 presents line graphs showing the effect of addition of at least one DP of ORC on the antibiotic activity of rifampin at various concentrations of the rifampin: 0.25 μg/ml (upper left panel), 0.125 μg/ml (upper middle panel), 0.062 μg/ml (upper right panel), 0.015 μg/ml (lower left panel), 0.031 μg/ml (lower middle panel), and 0 μg/ml (PBS control; lower right panel).

FIG. 3 presents line graphs showing the effect of addition of DP of ORC on the antibiotic activity of clindamycin at various concentrations of the clindamycin: 0.25 μg/ml (upper left panel), 0.125 μg/ml (upper middle panel), 0.065 μg/ml (upper right panel), 0.032 μg/ml (lower left panel), and 0 μg/ml (PBS control; lower right panel).

FIG. 4 presents line graphs showing the effect of addition of at least one DP of ORC on the antibiotic activity of gentamycin, at various concentrations of the gentamycin: 1 μg/ml (upper left panel), 0.1 μg/ml (upper middle panel), 0.5 μg/ml (upper right panel), 0.3 μg/ml (lower left panel), 0.1 μg/ml (lower middle panel), and 0 μg/ml (PBS control; lower right panel).

FIG. 5 presents line graphs showing the effect of addition of at least one DP of ORC on the antibiotic activity of tetracycline, at various concentrations of the tetracycline: 0.4 μg/ml (upper left panel), 0.2 μg/ml (upper middle panel), 0.1 µg/ml (upper right panel), 0.05 µg/ml (lower left panel), 0.025 µg/ml (lower middle panel), and 0 µg/ml (PBS control, lower right panel).

FIG. 6 presents line graphs showing the antibiotic effect of at least one DP of ORC alone (Blank ORC DP; upper right panel) or at least one DP of ORC together with antibiotics as in FIGS. 1 to 5: gentamycin (upper left panel), tetracycline (upper middle panel), rifampin (lower left panel) clindamycin (lower middle panel), and minocycline (lower right panel) In this Figure "ORC" refers to ORC DP.

DESCRIPTION OF SOME EMBODIMENTS OF THE INVENTION

Figure 1:
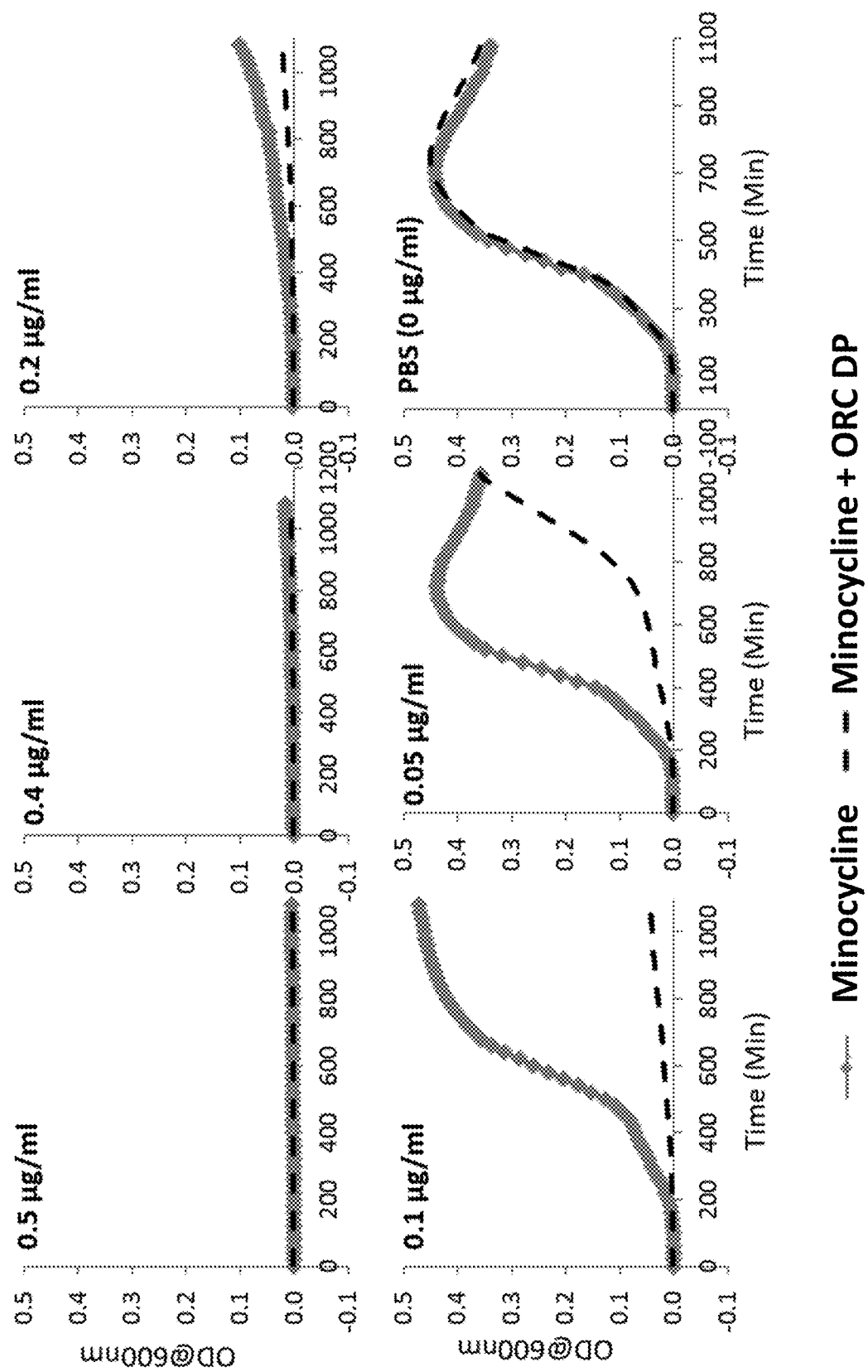
FIG. 1 presents line graphs showing the effect of addition of at least one degradation product (DP) of oxidized regenerated cellulose (ORC) on the antibiotic activity of minocycline, at various concentrations of the minocycline: 0.5 μg/ml (upper left panel), 0.4 μg/ml (upper middle panel), 0.2 μg/ml (upper right panel), 0.1 μg/ml (lower left panel), 0.05 μg/ml (lower middle panel), and 0 μg/ml (PBS control; lower right panel); PBS: phosphate-buffered saline.

The invention, in some embodiments thereof, relates to a composition comprising minocycline and at least one degradation product of OC, methods of preparation thereof and uses thereof. In some embodiments, the OC comprises ORC.

The principles, uses and implementations of the teachings herein may be better understood with reference to the accompanying description. Upon perusal of the description, one skilled in the art is able to implement the invention without undue effort or experimentation.

Before explaining at least one embodiment in detail, it is to be understood that the invention is not necessarily limited in its application to the details of construction and the arrangement of the components and/or methods set forth in the following description. The invention is capable of other embodiments or of being practiced or carried out in various ways. The phraseology and terminology employed herein are for descriptive purpose and should not be regarded as limiting.

As shown in the Examples below, the present inventors conducted as a primary stage a preliminary minimal inhibitory concentration (MIC) test for minocycline, in order to confirm the antibiotic effect of minocycline on the bacterial strains tested. Serial dilutions of the antibiotic were prepared and the MIC was determined as the dilution at which visible growth of bacteria was first seat. The MIC for *S. aureus* was found to be 0.25 µg/ml, which is consistent with the MIC values reported in the literature (0.06-0.5 µg/ml).

Following establishment of the MIC, the present inventors studied the interaction between degradation products of ORC and minocycline by incubating the minocycline at a concentration equal to or lower than the MIC, in the presence or absence of degradation products of ORC. Upon addition of a small amount of degradation products of ORC to the growth medium, the antimicrobial activity of minocycline was significantly enhanced, resulting in an MIC of 0.05 µg/ml.

Pads of dimensions of approximately 1×1.5 inch, weighing between 65-75 mg (70 mg on average) were used as a source of degradation products of ORC. The levels of degradation products of ORC obtained and used did not show intrinsic antimicrobial activity and the antimicrobial activity obtained with the combination could not be attributed to the effect of degradation products of ORC alone or to an additive effect of degradation products of ORC with minocycline.

In addition, any acidifying effect of the ORC during and/or after degradation was buffered, such as by adding a buffering agent to the composition, thereby forming an isotonic non-acidic medium for the bacteria to grow in.

When antibiotics other than minocycline were tested in combination with degradation products of ORC, no enhancement of antibiotic activity was seen. In fact, some tested antibiotics (such as gentamycin and rifampin) showed a reduction in the antibiotic activity as compared to the antibiotic alone, indicating interference between the degradation products of ORC and antibiotic.

The synergistic effect between minocycline and degradation products of ORC persisted when additional antibiotics (rifampin and/or clindamycin), which did not themselves exhibit a synergistic effect with ORC, were added to the mixture of minocycline and degradation products of ORC. Moreover, the inclusion of such additional antibiotics resulted in a further increase of antibiotic activity, in addition to that seen with minocycline and degradation products of ORC. Use of such combinations of antibiotics provides a wide coverage of gram negative and gram-positive antibiotics.

Minocycline-impregnated ORC pads were then prepared by immersing ORC pads in solutions of minocycline dissolved in methanol, followed by drying, in order to determine the best minocycline concentrations to be used as a source of product comprising minocycline and degradation products of ORC.

MIC of 0.0126 µg/ml was obtained in the presence of degradation products of ORC, as compared to 0.25 ng/ml in the absence of degradation products of ORC (Table 1), the MIC being at least 5.8-fold lower in the presence of degradation products of ORC than that in their absence. The MIC of minocycline together with degradation products of ORC, when prepared using degradation of ORC impregnated with minocycline was 12.60 ng/ml, the MIC being at least 19.8-fold lower in the presence of degradation products of ORC than that in their absence. The MIC of minocycline with at least one more antibiotic together with degradation products of ORC, when prepared using degradation of ORC impregnated with minocycline and the at least one more antibiotic was 200-fold lower of the MIC for minocycline alone. For example, 1.26 ng/ml minocycline in combination with 38.96 ng/ml clindamycin (total 10.22 ng/ml antibiotic loaded) together with ORC degradation products (from antibiotic-impregnated ORC) is a sufficient level of antibiotic to provide a high level of antibiotic activity.

EXAMPLES

The present inventors aimed to identify a preferred antibiotic for use in the preparation of a product comprising an antibiotic and one or more degradation products of ORC, as well as to determine suitable concentrations of the selected antibiotic. A study was conducted in 3 stages as described below.

Materials and Methods

Materials

Tryptic Soy broth (TSB) was acquired from Hy-Labs, Rehovot, Israel (Catalog no. (Cat #) BP266/1009).

Mueller Hinton Broth II (MHBII) was acquired from Becton Dickinson, N.J., USA (Cat #BBL298268).

*Staphylococcus aureus* (*S. aureus*), Strain #6538 was acquired from ATCC.

ORC pads used were Surgicel® from Ethicon, Cat #1951.

Phosphate buffer Saline (PBS) was acquired from Biological Industries Ltd., Beit Haemek, Israel (Cat #20-023-1A).

0.8/0.2 µm syringe filters were acquired from Pall Corporation, N.Y., USA (Cat #: 4658).

Antibiotics were acquired from Tokyo Chemical Industry (TCI), Tokyo. Japan as follows: Minocycline (Cat #: M2288); Gentamycin (Cat #: G0383); Rifampin (Cat #: R0079); Clindamycin (Cat #: C2256); and Tetracycline (Cat #: 12525).

Sterile water (SW) used was milli-Q purified water subjected to sterilization using a 0.2-micron cellulose acetate filter.

Orbital shaker: Thermo Fisher sold under the trademark MaxQ™ 4450 Benchtop Orbital Shakers.

Methods

Preparation of Inoculum

An isolated colony of *S. aureus* bacteria was picked from a fresh streak plate no more than 1 week old). The colony was transferred into 3-4 ml of TSB and incubated overnight in an orbital shaker at 35° C.-37° C.

The following day, the turbidity of the actively-growing broth culture was adjusted with Calcium-adjusted Mueller Hinton broth II (MHBII) to be equivalent to that of a 0.5 McFarland standard ($1 \times 10^8$ CFU/ml). The broth culture was maintained under ambient conditions prior to use.

No more than 15 minutes prior to use, the culture was further diluted 20-fold in MHBII to obtain a final $5 \times 10^6$ CFU/ml stock suspension.

Preparation of Extracts of Degradation Products of ORC

ORC pads undergo hydrolyzation, resulting in degradation products, when immersed in an aqueous solution. At least some degradation products of ORC are present in the form of particles which might interfere with OD readings and provide inaccurate results. In order to avoid this, degradation products were obtained as extracts from the ORC pads as described below and used in the present study.

a. Preparation of Blank Extract Comprising Degradation Products of ORC

ORC pads which had not been impregnated with antibiotic (referred to herein as "blank ORC pads"), were subjected to extraction and degradation in PBS for three hours at ambient temperature. Extract obtained from these blank ORC pads is referred to herein as "blank extract of degradation products of ORC".

b. Preparation of Extracts of Degradation Products of Blank ORC in Antibiotic

Blank ORC pads were subjected to extraction and degradation in a solution of antibiotic in PBS. Extracts of degradation products obtained from blank ORC pads in a solution of antibiotic in PBS is referred to herein as "extracts of degradation products of blank ORC in antibiotic".

Due to the acidity of ORC, which provides some antibiotic effect, the size of the pad used was small i.e. approximately 1×15 inch, weighing between 65-75 mg (70 mg on average) in order to prevent the ORC from affecting the final pH of live assay and therefore the growth of the bacteria.

15 ml tubes, each containing 3 ml of an antibiotic solution at a known concentration in sterile PBS, were prepared in duplicate.

Blank ORC pads were subjected to extraction and degradation in the antibiotic solution by immersing the ORC pads in the antibiotic solution for 3-5 hours at ambient temperature on a roller mixer (Stuart. Cat #SRT9D).

The extracted fluid comprising degradation products of ORC was filtered using 0.8/0.2 μm syringe filters (Pall, Cat #4658) and mixed with calcium-adjusted MHBII to provide antibiotic-ORC test suspension.

c. Preparation of Extract of Degradation Products of Antibiotic-Impregnated ORC

Solutions comprising different concentrations of antibiotics to be tested were prepared in methanol.

Blank ORC pads of dimensions 1×1.5 inch, weighing between 65-75 mg (70 mg on average), in duplicate, were immersed in the antibiotic solutions and then dried using a rotary evaporator to provide extract of degradation products of antibiotic-impregnated ORC pads.

15 ml test tubes containing 3 ml of sterile PBS were prepared, and the antibiotic-impregnated ORC pads were immersed in the tubes and incubated for 3-5 hours at ambient temperature on a roller mixer (Stuart. Cat #SRT9D).

Each of the above extracts w as filtered out using a sterile 0.8/0.2 μm syringe filter into a clean 15 ml tube. These extraction fluids are referred to herein as "extract of degradation products of antibiotic-impregnated ORC".

Example 1: Primary Stage Determination of Antibiotic MIC

The purpose of this stage was to confirm antibiotic activity according to MIC levels reported in the literature, to establish specific activity for the antibiotic, and to identify the preferred antibiotic for further studies Antibiotics tested were minocycline, rifampin, clindamycin, gentamycin and tetracycline.

MIC Measurement

The method used in this stage was based on the classic Minimum Inhibitory Concentration (MIC) measurements, as described by the Clinical and Laboratory Standards Institute (CLSI) document M07-A9: "Method for Dilution Antimicrobial Susceptibility Test for Bacteria that Grow Aerobically". While classic MIC measurements require visual inspection of plates for bacterial growth after 18 hours, growth was monitored in the present study according to optical density (OD) at 600 nm, using an ELISA reader (MultiSkan™) FC ELISA reader, Thermo Fisher Scientific, Mass., USA), thereby obtaining bacterial growth curves for tested antibiotic solutions.

A 96-well assay plate layout (Corning Cat 35%) was prepared as follows:

Columns 1 and 3-12: 100 μl of MHBII alone was added to each well.

Row 2: 200 μl of a solution of antibiotic in MHBII at the highest concentration to be tested was added to each well.

A series of 2-fold dilutions was performed, wherein 100 μl of solution of antibiotic was withdrawn from each well of column 2, transferred to the corresponding well of column 3, and mixed.

The dilution was then repeated by transfer from column 3 to column 4, and so on, until column 11, when the 100 μl of solution of antibiotic withdrawn front each well of column 11 was discarded.

The $5 \times 10^6$ CFU/ml stock suspension which had been prepared in advance w as transferred into a reservoir and 10 μl of the stock suspension were added into each well of columns 2-11 using a multichannel pipette to obtain a final $5 \times 10^5$ CFU/ml suspension.

The plate was then incubated at 37° C. with shaking in the ELISA reader and the optical density at 600 nm was read every 20 minutes for a total of 18 hours.

The average OD reading obtained for each antibiotic concentration was calculated and plotted against time to obtain a growth curve.

The MIC was determined as the first antibiotic concentration at which some bacterial growth occurred by the end of the 18-hour period.

Results

Results are presented in Table 1 below

TABLE 1

| Antibiotic Conc. (μg/ml) | MIC values for S. aureus according to the literature | MIC values found in the present study |
| --- | --- | --- |
| Rifampin | 0.004-0.015 | 0.015 |
| Clindamycin | 0.06-0.25 | 0.062 |
| Minocycline | 0.06-0.5 | 0.25 |
| Gentamicin | 0.12-1 | 0.25 |
| Tetracycline | 0.06-0.5 | 0.06 |

As seen in Table 1, the MIC values obtained in the present study were consistent with those published by the scientific literature.

Example 2: Secondary Stage Determination of Interaction of Antibiotic with Degradation Product(s) of OC This stage comprised MIC measurements for several antibiotics, either alone or in combination with degradation products obtained from ORC, in order to identify any interference of enhancement of the antibiotic activity in the presence of degradation products of ORC as evidenced by changes in MIC levels for the antibiotic.

MIC Measurement

The preferred antibiotic concentrations, as established in the first stage, were used for antibiotics in combination with the degradation products of ORC pads.

The various antibiotics tested and the concentrations used are shown in Table 2 below.

TABLE 2

| Antibiotic | Conc. 1 (μg/ml) | Conc. 2 (μg/ml) | Conc. 3 (μg/ml) | Conc. 4 (μg/ml) | Conc. 5 (μg/ml) | MIC determined in Example 1 (μg/ml) |
| --- | --- | --- | --- | --- | --- | --- |
| Minocycline | 0.5 | 0.4 | 0.2 | 0.1 | 0.05 | 0.25 |
| Rifampin | 0.11 | 0.055 | 0.028 | 0.014 | 0.007 | 0.015 |
| Clindamycin | 0.25 | 0.125 | 0.062 | 0.031 | N/A | 0.062 |
| Gentamicin | 11 | 0.8 | 0.5 | 0.3 | 0.1 | 0.75 |
| Tetracycline | 0.4 | 0.2 | 0.1 | 0.05 | 0.025 | 0.06 |

Blank extract of degradation products of ORC and extract in antibiotic of degradation products of ORC, prepared as described above, were diluted 10 folds in MHBII in sterile 15 ml capped tubes.

The $5 \times 10^6$ CFU/ml stock suspension which had been prepared in advance was transferred into a reservoir and 10 μl of the stock suspension were added into each well of columns 2-11 using a multichannel pipette to obtain a final $5 \times 10^5$ CFU/ml suspension.

TABLE 3

The plate layout used is shown in Table 3 below.

| | 1 | 2 | 3 | 4 | 5 | 6 | 7 | 8 | 9 | 10 | 11 | 12 |
| --- | --- | --- | --- | --- | --- | --- | --- | --- | --- | --- | --- | --- |
| A | SW | SW | SW | SW | SW | SW | SW | SW | SW | SW | SW | SW |
| B | SW | BLANK | Ab Conc. 1 + ORC | Ab Conc. 1 + ORC | Ab Conc. 1 + ORC | Ab Conc. 1 + ORC | Ab Conc. 1 | Ab Conc. 1 | Ab Conc. 1 | Ab Conc. 1 | W/O | SW |
| C | SW | BLANK | Ab Conc. 2 + ORC | Ab Conc. 2 + ORC | Ab Conc. 2 + ORC | Ab Conc. 2 + ORC | Ab Conc. 2 | Ab Conc. 2 | Ab Conc. 2 | Ab Conc. 2 | W/O | SW |
| D | SW | BLANK | Ab Conc. 3 + ORC | Ab Conc. 3 + ORC | Ab Conc. 3 + ORC | Ab Conc. 3 + ORC | Ab Conc. 3 | Ab Conc. 3 | Ab Conc. 3 | Ab Conc. 3 | W/O | SW |
| E | SW | BLANK | Ab Conc. 4 + ORC | Ab Conc. 4 + ORC | Ab Conc. 4 + ORC | Ab Conc. 4 + ORC | Ab Conc. 4 | Ab Conc. 4 | Ab Conc. 4 | Ab Conc. 4 | W/O | SW |
| F | SW | +ve Ctrl. | Ab Conc. 5 + ORC | Ab Conc. 5 + ORC | Ab Conc. 5 + ORC | Ab Conc. 5 + ORC | Ab Conc. 5 | Ab Conc. 5 | Ab Conc. 5 | Ab Conc. 5 | +ve Ctrl. | SW |
| G | SW | +ve Ctrl. | PBS-ORC | PBS-ORC | PBS-ORC | PBS-ORC | PBS | PBS | PBS | PBS | +ve Ctrl. | SW |
| H | SW | SW | SW | SW | SW | SW | SW | SW | SW | SW | SW | SW |

150 μl sterile water (SW) was added to each of the border wells (i.e. columns 1 and 12, rows A and H) in order to prevent any drying effect for the duration of the experiment.

Column 2, rows B to E were left as blanks, i.e. containing no antibiotics without bacteria, in order to provide a reference for the basic OD of the plate.

Columns 3 to 6, rows B to F, were filled with the Blank ORC extracted in antibiotic at decreasing concentrations 1 to 5, diluted 10 folds in MHBII. Each sample tested was placed in 4 well repeats for statistical results.

Columns 7 to 10, rows B to F, were filled with the antibiotic solution (AB) at decreasing concentrations 1 to 5, diluted 10 folds in MHBII Each sample tested was placed in 4 well repeats for statistical results.

Columns 2 and 11, rows F and G, contained as a positive control (+ve) antibiotic alone, at low and high concentrations, prepared from a stock solution of the test antibiotic in PBS, diluted in sterile MHBII.

Columns 3 to 6, row G, were filled with the blank extract of degradation products of ORC (PBS-ORC) diluted 10 folds in MHBII. These samples were used as a negative control in order to ascertain that the bacteria were not significantly affected by the degradation products of ORC alone and that any bacterial growth impairment detected was due to the effect of the antibiotic Columns 7 to 10, row G, were filled with PBS alone (diluted 10-fold in MHBII, as a further negative control.

Column 11, rows B to E, contained a further negative control comprising with bacteria and no antibiotic (MHBII) providing the bacterial growth performance in these conditions without any antibacterial interference (W/O).

At least 4 wells contained bacteria alone in MHBII in order to verify that no interference in bacterial growth occurred.

The plate was incubated at 37° C. with shaking in the ELISA reader and the optical density at 600 nm was read every 20 minutes for a total of 18 hours.

The average and standard deviation for OD readings was calculated for each time point of the wells using Excel. The average values were plotted against time to obtain a graph of the bacterial growth curves in the presence of each of the antibiotics tested.

In some cases, the average OD was plotted for a single endpoint of 800 minutes for the various antibiotic treatments and controls. The endpoint of 800 minutes was selected as this was found to be the time at which the difference between the various antibiotic concentrations is greatest.

The average values were also entered into the GraphPad Prism program (GraphPad Software Inc., Calif., USA) in order to calculate the Effective Time 50 (ET50) i.e. the time, in minutes, required for the antibiotic to induce a response halfway between the baseline and maximum, where the maximum is the bacterial growth in MHBII with PBS. This provides a quantifiable measure of the efficacy of the antibiotics tested and enables comparison of the various samples tested. It is noted that ET50 values of above 1650 are indicative of high antibiotic activity while ET50 values of greater than 2000 minutes were found to be imprecise and are therefore regarded as maximal growth inhibition. The range of 1000 to 1650 is indicative of positive antibiotic activity. In cases wherein there was such limited growth that an ET50 value could not be established, the result is indicated as N/A.

In order to compare different antibiotic concentrations, the average OD at 800 minutes for each sample tested was plotted against the antibiotic concentration and the EC50 calculated i.e. the concentration of antibiotic which induces a response halfway between the baseline and maximum after a specified exposure time.

Results
a. Minocycline

Results are shown in Table 4 below and in FIG. 1, wherein ORC refers to degradation products of ORC.

TABLE 4

| Minocycline concentration | 0 µg/ml | | 0.05 µg/ml | | 0.1 µg/ml | | 0.2 µg/ml | | 0.4 µg/ml | | 0.5 µg/ml | |
|---|---|---|---|---|---|---|---|---|---|---|---|---|
| | − ORC | + ORC | − ORC | + ORC | − ORC | + ORC | − ORC | + ORC | − ORC | + ORC | − ORC | + ORC |
| ET50 | 411.7 | 423.6 | 428.1 | 901.1 | 555.1 | >2000 | 1771 | >2000 | >2000 | >2000 | >2000 | >2000 |

The results show that addition of degradation product(s) of ORC to minocycline resulted in a strong synergistic effect. The effect was greater at lower concentrations of minocycline, where the antibiotic activity of minocycline alone was low.

For example, 0.05 µg/ml minocycline alone had no antibiotic effect alone (ET50 428.1 minutes, which is very similar to the ET50 value of 411.7 minutes obtained in the absence of minocycline). Following addition of ORC degradation product(s) to the minocycline solution, the ET50 was increased to 901 minutes.

A similar effect was seen with minocycline concentrations of 0.1 µg/ml of (ET50 of 555 and over 2000 in the absence and presence, respectively, of ORC) and 0.2 µg/ml (ET50 of 1771 and over 2000 in the absence and presence, respectively, of ORC).

Since 0.4 µg/ml of minocycline alone showed an ET50 of above 2000 minutes, such that maximal growth inhibition was shown, the addition of degradation product(s) of ORC to the antibiotic solution did not produce any increase in antibiotic effect.

Degradation products of ORC alone, in the amount used, did not show any antibiotic effect.

b. Rifampicin (Rifampin)

Figure 2:
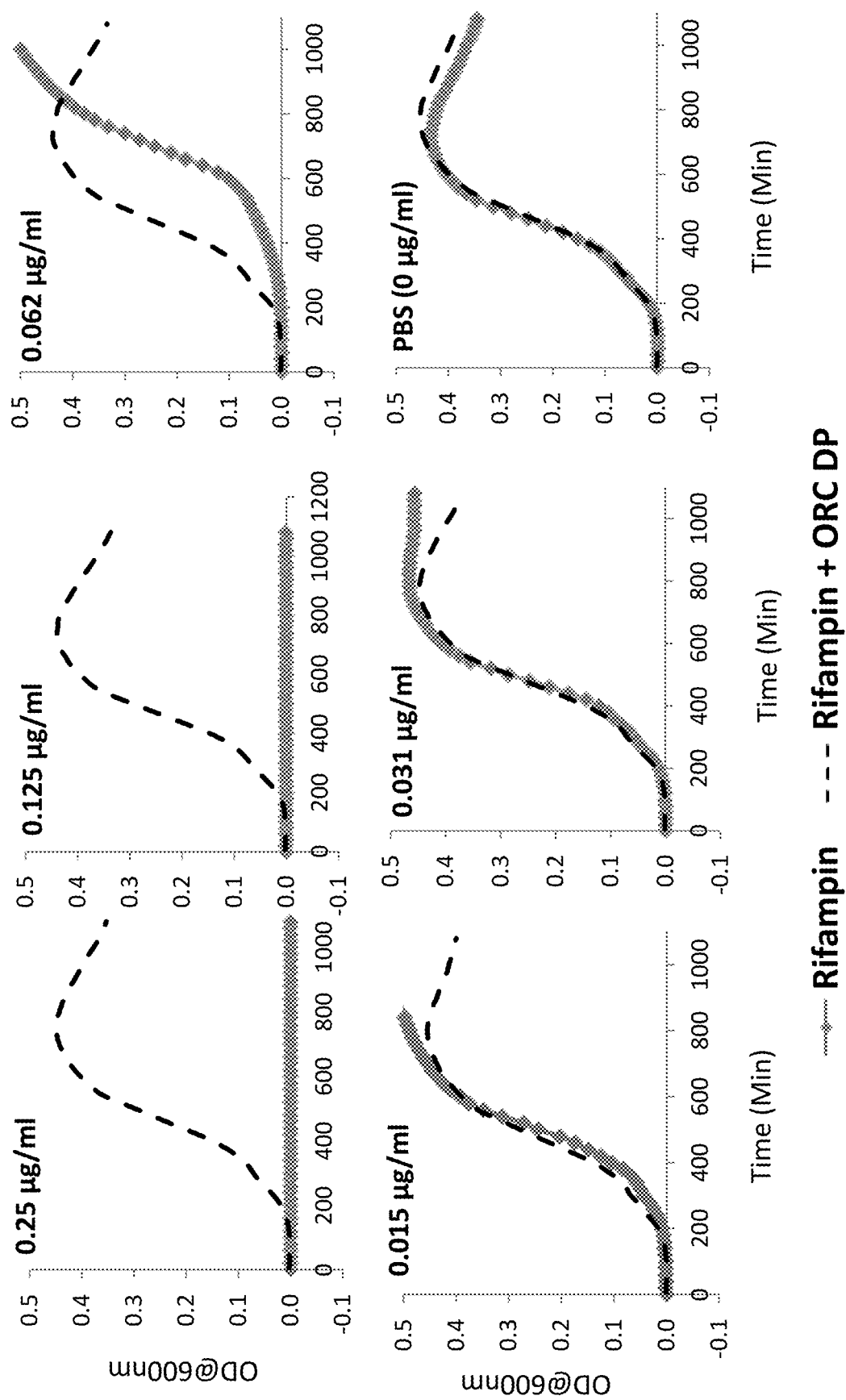

Results are shown in Table 5 below and in FIG. 2, wherein ORC refers to degradation product(s) of ORC.

TABLE 5

| Rifampin Concentration | 0 µg/ml | | 0.015 µg/ml | | 0.031 µg/ml | | 0.062 µg/ml | | 0.125 µg/ml | | 0.25 µg/ml | |
|---|---|---|---|---|---|---|---|---|---|---|---|---|
| | − ORC | + ORC | − ORC | + ORC | − ORC | + ORC | − ORC | + ORC | − ORC | + ORC | − ORC | + ORC |
| ET50 | 424.9 | 432.8 | 470.7 | 440.5 | 448.4 | 436.3 | 669.1 | 432.8 | N/A | 432.3 | N/A | 430.8 |

The results show that degradation products of ORC interfere with the antibiotic activity of rifampin, such that no antibiotic activity was seen upon addition of degradation products of ORC to solutions of rifampin at concentrations which showed antibiotic activity when used alone.

For example, at concentrations of 0.25 µg/ml and 0.125 µg/ml rifampin alone there was no growth at all (no ET50 values were therefore available). However, once degradation products of ORC were added to the rifampin solutions, the growth profile resembled that of the control (ET50 values of around 430 minutes). At a concentration of 0.062 µg/ml rifampin, delayed bacterial growth was seen (ET50 of 669.1), but the antibiotic activity was decreased by the addition of degradation products of ORC, reducing the ET50 value to 430 minutes.

c. Clindamycin

Figure 3:
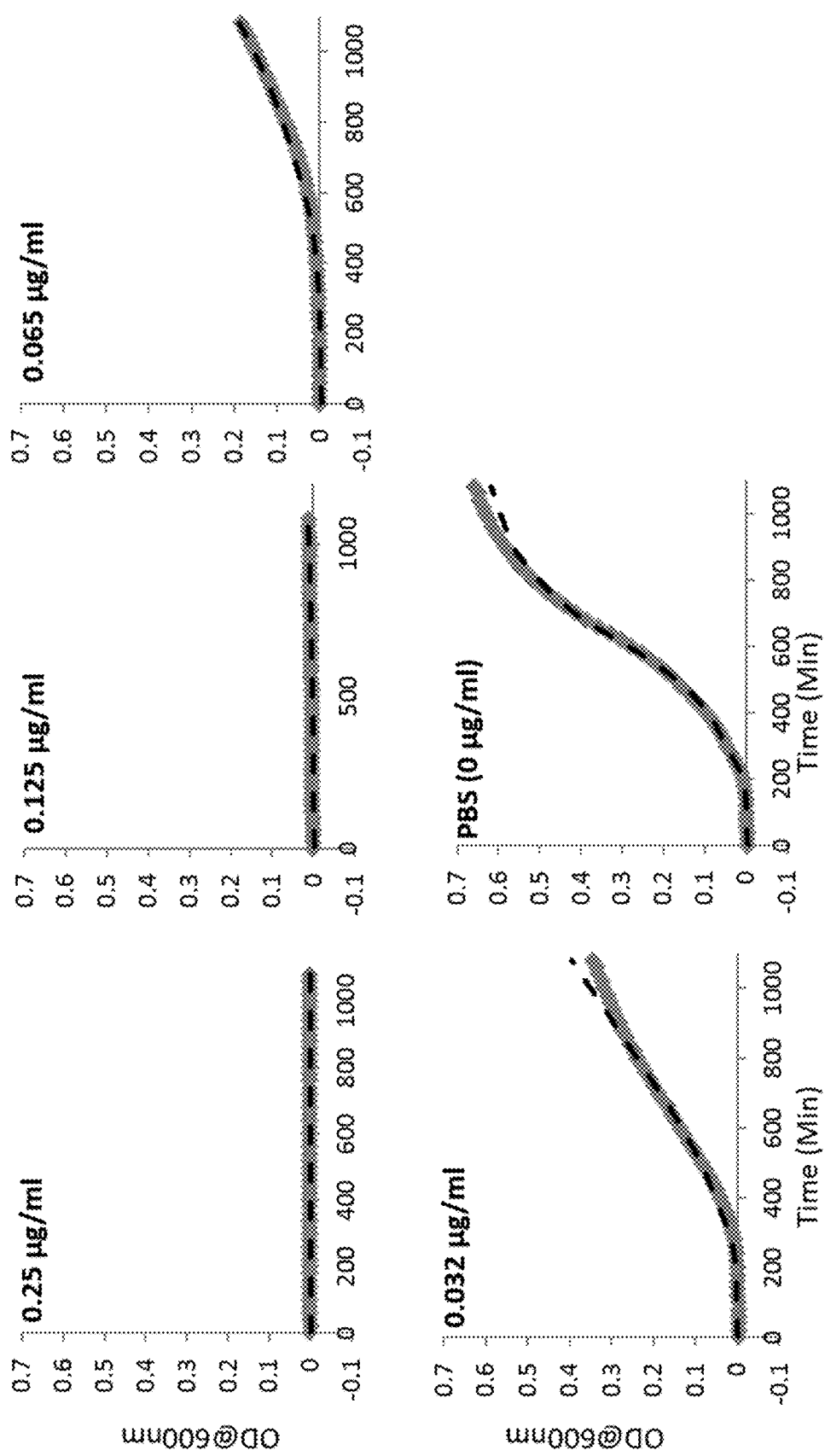

Results are shown in Table 6 below and in FIG. 3, wherein ORC refers to degradation products of ORC.

TABLE 6

| Clindamycin concentration | 0 µg/ml | | 0.03125 µg/ml | | 0.0625 µg/ml | | 0.125 µg/ml | | 0.25 µg/ml | |
|---|---|---|---|---|---|---|---|---|---|---|
| | − ORC | + ORC | − ORC | + ORC | − ORC | + ORC | − ORC | + ORC | − ORC | + ORC |
| ET50 | 650.2 | 648 | 1001 | 1049 | 1494 | 1432 | >2000 | >2000 | N/A | N/A |

The results show that addition of degradation products of ORC had no effect on the antibiotic activity of clindamycin at the clindamycin concentrations tested.

d. Gentamycin

Figure 4:
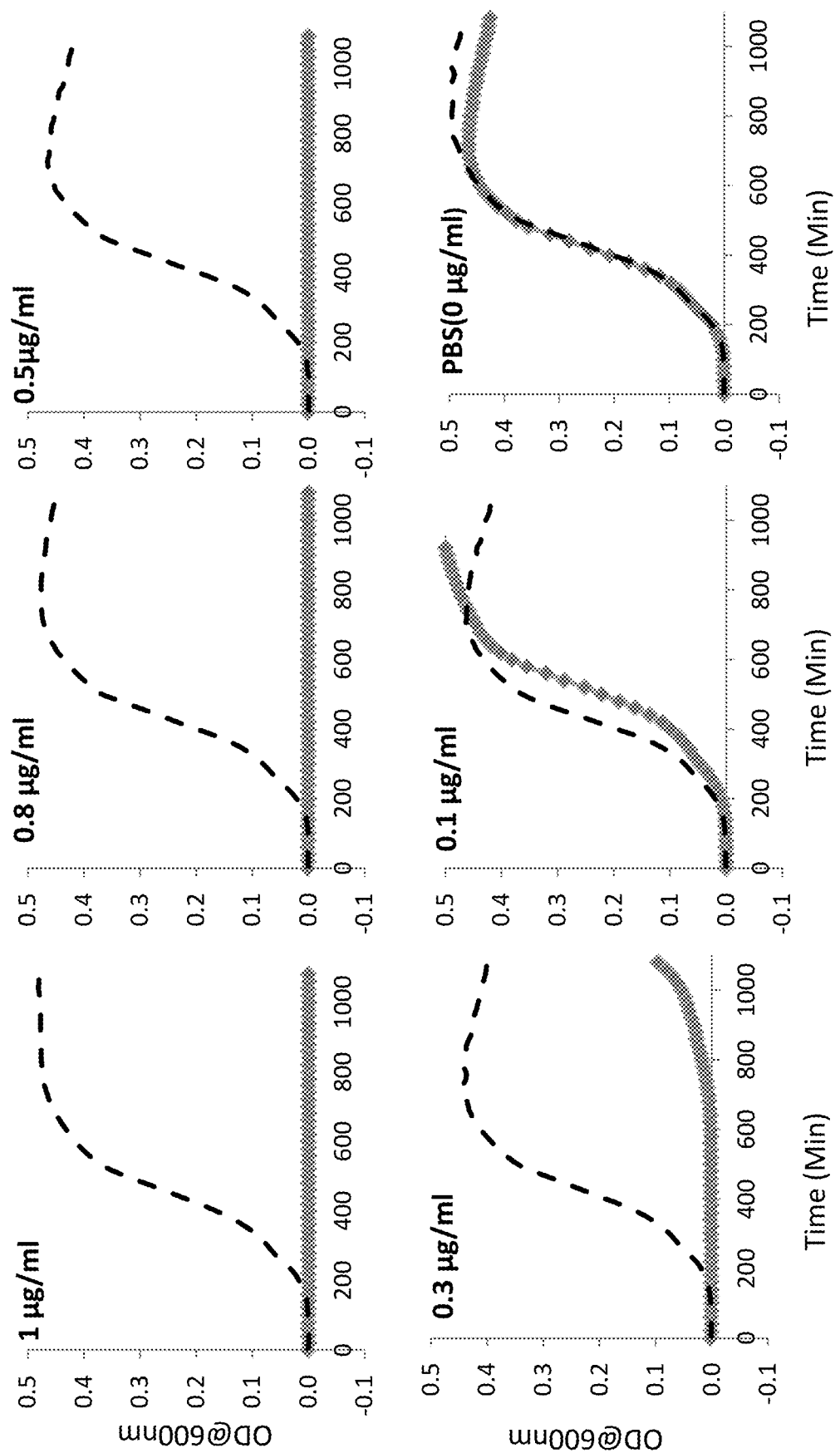

Results are shown in Table 7 below and in FIG. 4, wherein ORC refers to degradation products of ORC.

TABLE 7

| Gentamycin Conc. | 0 µg/ml | | 0.1 µg/ml | | 0.3 µg/ml | | 0.5 µg/ml | | 0.8 µg/ml | | 1 µg/ml | |
|---|---|---|---|---|---|---|---|---|---|---|---|---|
| | − ORC | + ORC | − ORC | + ORC | − ORC | + ORC | − ORC | + ORC | − ORC | + ORC | − ORC | + ORC |
| ET50 | 414.1 | 420.7 | 509.4 | 423.7 | 1360 | 429.3 | N/A | 423.1 | N/A | 422.7 | N/A | 446.6 |

The results show that addition of degradation products of ORC to solutions of gentamycin resulted in decreased antibiotic activity at all gentamycin concentrations tested.

e. Tetracycline

Figure 5:
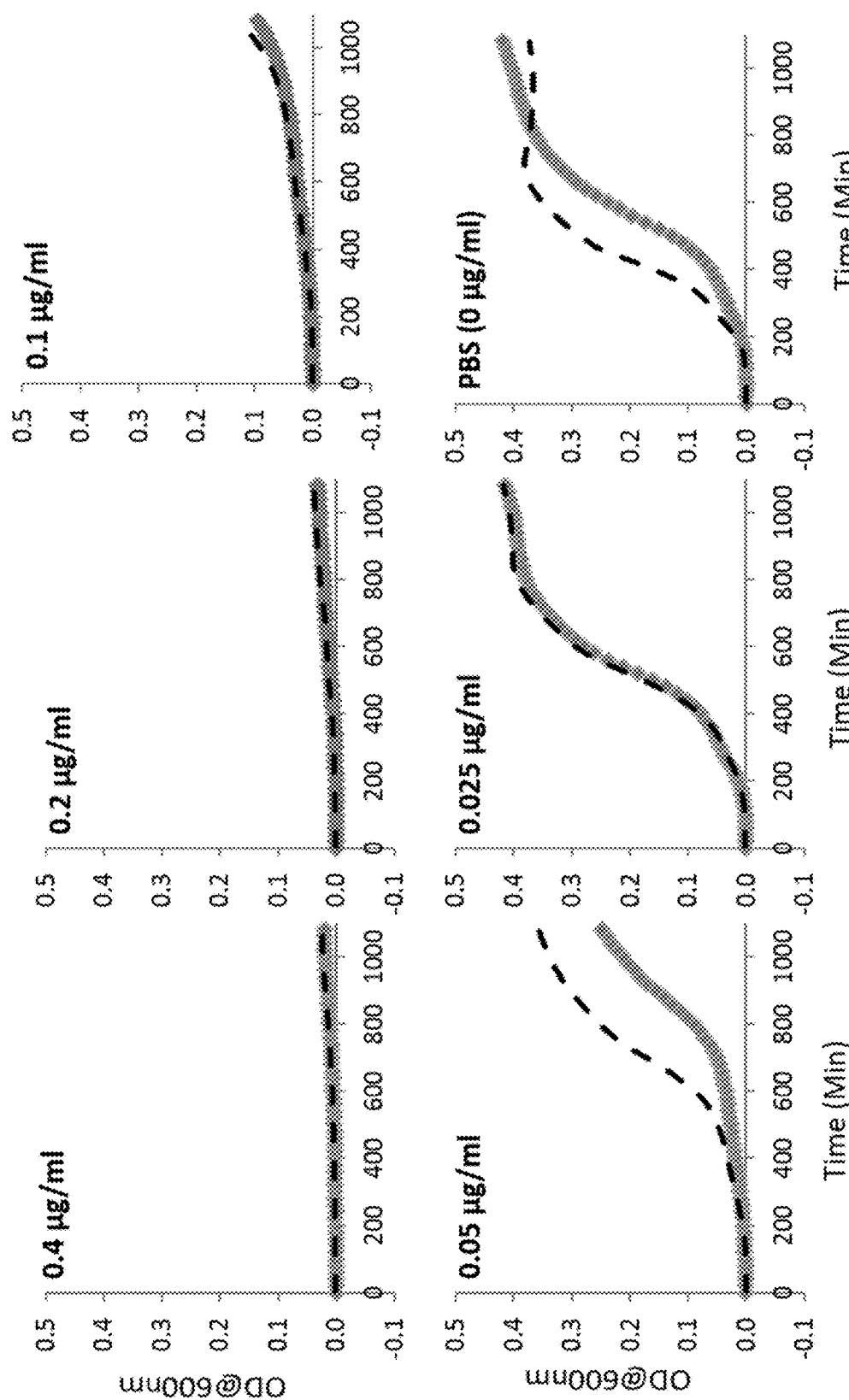

Results are shown in Table 8 below and in FIG. 5, wherein URC refers to degradation products of ORC.

TABLE 8

| Tetracycline Conc. | 0 µg/ml | | 0.025 µg/ml | | 0.05 µg/ml | | 0.1 µg/ml | | 0.2 µg/ml | | 0.4 µg/ml | |
|---|---|---|---|---|---|---|---|---|---|---|---|---|
| | − ORC | + ORC | − ORC | + ORC | − ORC | + ORC | − ORC | + ORC | − ORC | + ORC | − ORC | + ORC |
| ET50 | 565.6 | 425.3 | 531.1 | 517.7 | 989.9 | 741.1 | 1889 | 1470 | >2000 | >2000 | >2000 | >2000 |

The results show that addition of degradation products of ORC had no effect on the antibiotic activity of tetracycline at the tetracycline concentrations tested.

Figure 6:
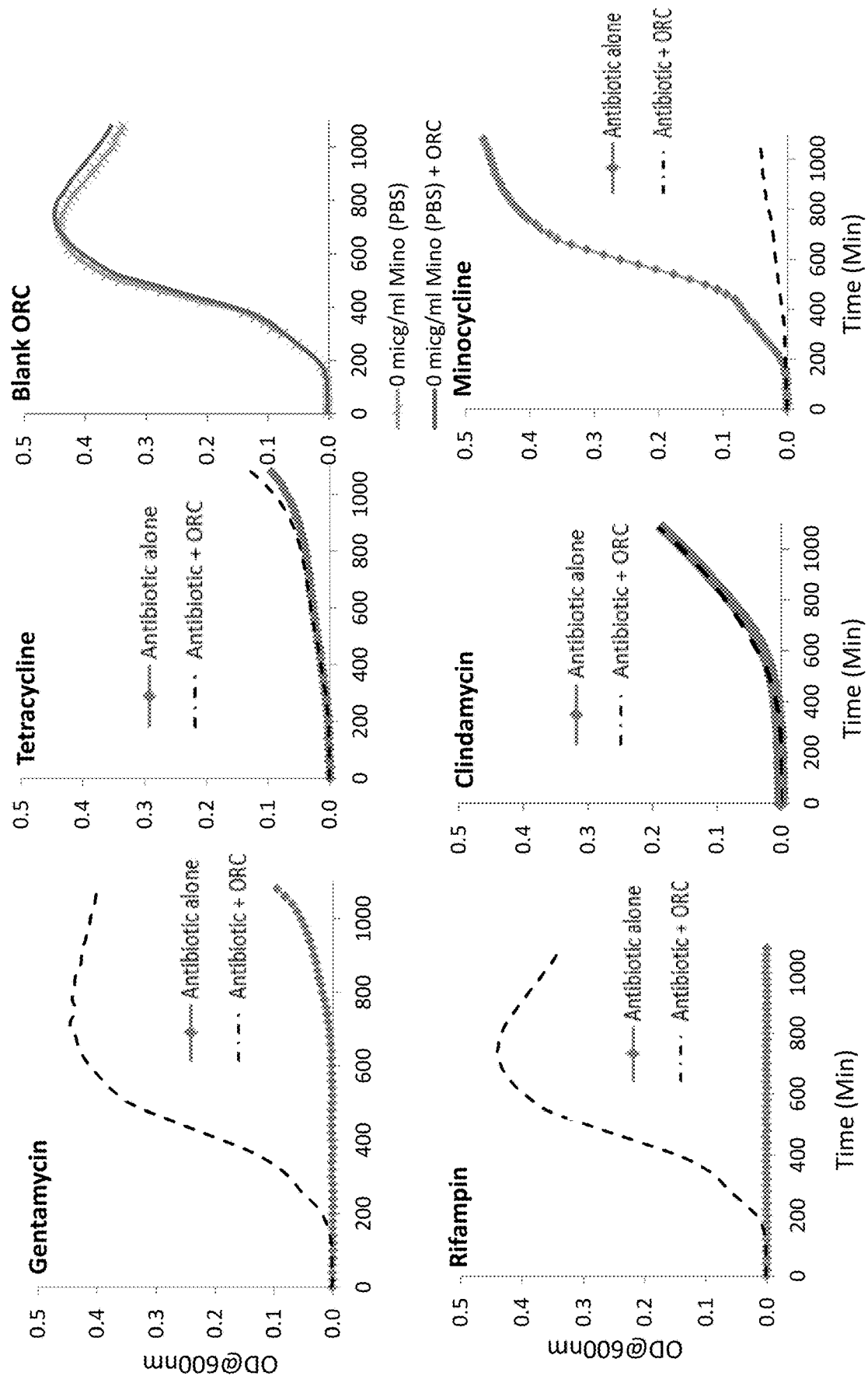

A summary of the results obtained for all the tested antibiotics is shown in FIG. 6. As shown in FIG. 6, the increase in OD after treatment with gentamycin and degradation products) of ORC, or rifampin and degradation products of ORC, respectively, was greater than that obtained after treatment with the antibiotic alone, indicating that interference occurred between the antibiotic and the degradation products of ORC in each case, such interference resulting in lowering of the antibiotic activity.

As shown in the lower and upper panels of the middle of FIG. 6, the increase in OD after treatment with clindamycin and degradation products of ORC or tetracycline and degradation products of ORC, respectively, was substantially the same as that obtained after treatment with the antibiotic alone, indicating that no interference occurred between clindamycin and degradation products of ORC or tetracycline and degradation product(s) of ORC.

As shown in the upper panel at the right of FIG. 6, the increase in OD after no minocycline treatment was substantially the same as that obtained with degradation products of ORC alone.

As shown in FIG. 6, the decrease in OD after treatment with minocycline together with ORC degradation products was significantly greater than that obtained after treatment with either degradation products of ORC or the antibiotic alone, indicating that a synergistic effect occurred between minocycline and degradation products of ORC.

Example 3. Tertiary Stage-Determination of Antimicrobial Activity of Degradation Products of ORC Obtained from Extracts of Orc Pads Impregnated with a Single or Combination Antibiotic This stage comprised testing the antimicrobial activity of extract of degradation products of antibiotic-impregnated ORC pads in order to identify a suitable concentration range for single or multiple antibiotics in the antibiotic-impregnated ORC pads as a source of a product comprising antibiotic and degradation products of ORC for use in treatment of SSI.

Determination of Antibiotic Impregnation Levels

In order to determine the quantity of antibiotic impregnated into an ORC pad from which the extract of degradation products of antibiotic-impregnated ORC is to be obtained, the antibiotic was extracted out of the pad and the antibiotic levels were measured.

Impregnation was carried out as described above in section "Preparation of antibiotic impregnated ORC extracts" under "Methods". Briefly. ORC pads weighing on average 70 mg each were impregnated with the selected antibiotic.

Samples of pads impregnated with rifampin, minocycline and clindamycin, as well as blank ORC pads (w/o impregnated antibiotics) were taken for antibiotic loading analysis. Each sample was weighed and placed in a 15 ml scintillation vial and 1 ml of methanol was added.

The vials were hand shaken periodically and after 2 hours the methanol was decanted off for analysis ("1st extract"). A second 1 ml of methanol was added into the scintillation vial, and the process was repeated to obtain the "2nd extract". A third 1 ml of methanol was added into the scintillation vial, and the process was repeated to obtain the "3rd extract".

The 1st extract, 2nd extract, and the 3rd extract were then analyzed by LC/UV/MS using an Agilent 1260 Series UPLC with photodiode array detector and Agilent 1100 MSD mass spectrometer.

The concentration of the antibiotic in each extract of degradation products of antibiotic-impregnated ORC was estimated by using the calibration curve of corresponding standards (peak area at 350 nm for rifampicin; 425 and 458 peak area for clindamycin and minocycline, respectively).

Results are presented in Table 9 below.

TABLE 9

| Antibiotic | Impregnation Loading Solution Conc. (µg/ml) | Antibiotic Conc. per ORC pad (µg/g) | | | Total Antibiotic impregnation level in ORC pad (µg/g) |
|---|---|---|---|---|---|
| | | 1st extract | 2nd extract | 3rd extract | |
| Minocycline | 20 | 8.9 | 1.9 | <1.4 | 10.8 |
| Clindamycin | 10 | 10.7 | 2.1 | <1.4 | 12.8 |
| Rifampin | 200 | 409.2 | 139.0 | 79.9 | 628.2 |

The results presented in Table 9 were then used to calculate the amount of antibiotic loaded on the rest of the antibiotic-impregnated ORC pads to be for production of extract of degradation products of antibiotic-impregnated ORC used in the present studies. A linear dilution of the antibiotic was used in order to prepare the loading solution, a simple linear equation can be assigned in turn in order to deduct the level of antibiotic loaded onto the rest of the antibiotic impregnated pads.

ORC pads for production of degradation products of ORC were impregnated with a single antibiotic or with a combination of two antibiotics. The antibiotic loading onto each of the pads tested, calculated according to the loading levels described in Table 9, are depicted in Table 10 below.

Table 10 shows ORC impregnation levels deduced according to the impregnation levels found in Table 9 above and their consequent concentrations in the following MIC experiments (see section b).

TABLE 10

| | Impregnation Loading Solution Conc. (µg/ml) | Total antibiotic impregnation level in ORC pad (µg/g) | Total Antibiotic impregnation level in ORC pad (%) | Antibiotic concentration in MIC experiment (ng/ml) |
|---|---|---|---|---|
| Rifampin | 200 | 628.2 | 0.06282 | 1465.8 |
| | 150 | 471.15# | 0.047115 | 1099.35 |
| | 100 | 314.1 | 0.03141 | 732.9 |
| | 50 | 157.05 | 0.015705 | 366.45 |
| | 40 | 125.64 | 0.012564 | 293.16 |
| | 30 | 94.23 | 0.009423 | 219.87 |
| | 20 | 62.82 | 0.006282 | 146.58 |
| | 10 | 31.41 | 0.003141 | 73.29 |

TABLE 10-continued

| | Impregnation Loading Solution Conc. (µg/ml) | Total antibiotic impregnation level in ORC pad (µg/g) | Total Antibiotic impregnation level in ORC pad (%) | Antibiotic concentration in MIC experiment (ng/ml) |
|---|---|---|---|---|
| Clindamycin | 20 | 25.6 | 0.00256 | 59.73 |
| | 10 | 12.8 | 0.00128 | 29.87 |
| | 5 | 6.4 | 0.00064 | 14.93 |
| | 2.5 | 3.2 | 0.00032 | 7.47 |
| | 3 | 3.84 | 0.000384 | 8.96 |
| | 2 | 2.56 | 0.000256 | 5.97 |
| | 1.5 | 1.92 | 0.000192 | 4.48 |
| | 1 | 1.28 | 0.000128 | 2.98 |
| | 0.5 | 0.64 | 0.000064 | 1.49 |
| Minocycline | 40 | 21.6 | 0.00216 | 50.4 |
| | 20 | 10.8 | 0.00108 | 25.2 |
| | 10 | 5.4 | 0.00054 | 12.6 |
| | 5 | 2.7 | 0.00027 | 6.3 |
| | 4 | 2.16 | 0.000216 | 5.04 |
| | 3 | 1.62 | 0.000162 | 3.78 |
| | 2 | 1.08 | 0.000108 | 2.52 |
| | 1 | 0.54 | 0.000054 | 1.26 | a. Antimicrobial Activity of Degradation Products of ORC Pads Impregnated with Different Concentrations of a Single Antibiotic ORC pads impregnated with a single antibiotic to be used for preparation of degradation products of ORC were tested for antimicrobial activity using the MIC measurement described in Example 2 above. Briefly, ORC pads weighing on average 70 mg each were impregnated with the selected antibiotic. Extracts of degradation products of antibiotic-impregnated ORC were prepared by immersion and incubation in 3 ml of sterile PBS for 3 hours at ambient temperature. The ORC degeneration products were then removed, and any remaining ORC particles were filtered out using a 0.8/0.4 µm syringe filter. This extraction fluid was then diluted 10-fold into Muller Hinton growth medium containing bacteria. Bacterial growth was monitored every 20 min for a total of 18 hours according to optical density (OD) at 600 nm, using an ELISA reader.

Tables 11a summarizes the results obtained by the used degradation products of single antibiotic-impregnated ORC pads according to their ET50 as described in Example 2. The results resemble those of the secondary stage MIC see Example 2, and the synergistic effect of minocycline is even more pronounced when the antibiotic is impregnated onto the ORC, such that degradation products of antibiotic-impregnated ORC pads are obtained.

TABLE 11a

| | Antibiotic conc. in impregnation fluid | % antibiotic on ORC | conc. in MIC ng/ml | ET50 |
|---|---|---|---|---|
| Minocycline | 40 µg/ml I | 0.00216 | 50.40 | >2000 |
| | 20 µg/ml I | 0.00108 | 25.20 | >2000 |
| | 10 µg/ml II | 0.00054 | 12.60 | 2000 |
| | 5 µg/ml II | 0.00027 | 6.30 | 1145 |
| | 0 | 0 | 0 | 819.4 |
| Rifampin | 200 µg/ml | 0.06282 | 1465.8 | >2000 |
| | 150 µg/ml | 0.047115 | 1099.35 | >2000 |
| | 100 µg/ml | 0.03141 | 732.9 | 1396 |
| | 50 µg/ml | 0.015705 | 366.45 | 643 |
| | 0 | | | 712.5 |

TABLE 11a-continued

| | Antibiotic conc. in impregnation fluid | % antibiotic on ORC | conc. in MIC ng/ml | ET50 |
|---|---|---|---|---|
| Clindamycin | 20 µg/ml | 0.00256 | 59.73 | >2000 |
| | 10 µg/ml | 0.00128 | 29.87 | >2000 |
| | 5 µg/ml | 0.00064 | 14.93 | 1425 |
| | 2.5 µg/ml | 0.00032 | 7.47 | 975.9 |
| | 0 | 0 | 0 | 663.2 |

The MIC result presented in Table 11b below shows the reduction in the minocycline levels required in order to achieve antimicrobial activity. It is apparent that the interference of degradation products of ORC with Rifampin activity remains, generating an MIC which was 50 times higher than that of the primary stage MIC. The MIC of Clindamycin was four times lower in the ORC degradation products from the impregnated ORC. However, the MIC of Minocycline was 20 times lower than that of the $1^{st}$ stage MIC, further establishing the synergistic effect of minocycline and degradation products of ORC.

The results showed that the impregnation process did not impair the synergism of minocycline and degradation products of ORC described above, and that rifampin, the activity of which was detected as impaired, was also impaired once impregnated onto the ORC. These results provide further proof of the synergism between degradation products of ORC and Minocycline.

TABLE 11b

| Antibiotic# | In-house (primary)MIC (µg/ml) # | Antibiotic-impregnated ORC (tertiary) MIC (µg/ml)# | Fold reduction in MIC concentration |
|---|---|---|---|
| Minocycline# | 0.254# | 0.0126# | 19.85# |
| Rifampin# | 0.015# | 0.733# | 0.019# |
| Clindamycin# | 0.0624# | 0.015# | 4.15# | c. Antimicrobial Activity of Degradation Products of ORC Pads Impregnated with Different Concentrations of a Combination of Two Antibiotics Since a synergistic effect was observed between degradation products of ORC and minocycline, minocycline was used in all combination studies. Combinations of: 1—minocycline and clindamycin; or 2—minocycline and rifampin were studied, as shown in Table 12 below.

TABLE 12

| Minocycline ng/ml | Rifampin ng/ml | Total (ng/ml) | ET50 |
|---|---|---|---|
| 0.00 | 0.00 | 0.00 | 409 |
| 1.26 | 0.00 | 1.26 | 585.4 |
| 2.52 | 0.00 | 2.52 | 799.9 |
| 5.04 | 0.00 | 5.04 | >2000 |
| 6.30 | 0.00 | 6.30 | >2000 |
| 0.00 | 73.29 | 73.29 | 406.8 |
| 1.26 | 73.29 | 74.55 | 606.8 |
| 6.30 | 73.29 | 79.59 | 1264 |
| 0.00 | 146.58 | 146.58 | 442.3 |
| 2.52 | 146.58 | 149.10 | 881.2 |
| 5.04 | 146.58 | 151.62 | 1992 |
| 0.00 | 293.16 | 293.16 | 450.4 |
| 2.52 | 293.16 | 295.68 | 1482 |
| 5.04 | 293.16 | 298.20 | >2000 |
| 0.00 | 366.45 | 366.45 | 418.1 |
| 1.26 | 366.45 | 367.71 | >2000 |
| 6.30 | 366.45 | 372.75 | >2000 |

TABLE 12-continued

| Minocycline ng/ml | Clindamycin ng/ml | Total ng/ml | ET50 |
|---|---|---|---|
| 0.00 | 0.00 | 0.00 | 434.8 |
| 1.26 | 0.00 | 1.26 | 637.6 |
| 2.52 | 0.00 | 2.52 | 1072 |
| 5.04 | 0.00 | 5.04 | >2000 |
| 6.30 | 0.00 | 6.30 | >2000 |
| 0.00 | 1.49 | 1.49 | 448.7 |
| 1.26 | 1.49 | 2.75 | 734.5 |
| 6.30 | 1.49 | 7.79 | >2000 |
| 0.00 | 2.99 | 2.99 | 485.1 |
| 2.52 | 2.99 | 5.51 | 1227 |
| 5.04 | 2.99 | 8.03 | >2000 |
| 0.00 | 5.97 | 5.97 | 521.1 |
| 2.52 | 5.97 | 8.49 | 1488 |
| 5.04 | 5.97 | 11.01 | >2000 |
| 0.00 | 8.96 | 8.96 | 579.8 |
| 1.26 | 8.96 | 10.22 | 1650 |
| 6.30 | 8.96 | 15.26 | >2000 |

Since the study included many possible combinations of two antibiotics, each with their own different concentration range, a matrix of possible antibiotic concentrations was designed, and degradation products of ORC were prepared accordingly (see Table 10). Since all the possible combinations could not be fitted into one 96 well plate, a series of MIC experiments were carried out. In order to compare between the different plates and obtain results which can provide information regarding the activity of the all antibiotics and concentrations tested, ET50 values (as described in Example 2) were used, which provided a quantitative measurement of the antibiotic activity which could be used to compare results from different assay plates.

Table 12 presents ET50 results for combinations of minocycline with rifampin or minocycline with clindamycin at different concentrations. The results show that 6.3 ng/ml minocycline in combination with 366.45 ng/ml rifampin (total 372.75 ng/ml antibiotic loaded), as well as 1.26 ng/ml minocycline in combination with 38.96 ng/ml clindamycin (total 10.22 ng/ml antibiotic loaded) is a sufficient level of antibiotics which provides a great antibiotic activity. In addition, a combination of 2.52 ng/ml minocycline with 293.16 ng/ml rifampin as well as 2.52 ng/ml minocycline with 0.5.97 ng/ml of clindamycin also provided a high level of antibiotic activity.

The primary stage study confirmed that no false positive antibacterial activity occurred, that the baseline antibacterial activity of the reagents and bacterial strains used was correct. The MIC obtained for S. aureus using a specific antibiotic alone was found to be consistent with values published in known literature.

In the secondary stage, it was shown that although it is reported that ORC itself has some intrinsic antimicrobial activity (Dineen P. "The effect of oxidized regenerated cellulose on experimental infected splenotomies" Journal of Surgical Research 1977; 23: 114-116); the amount of ORC degradation products used in the present study was ineffective in providing bacterial growth inhibition as determined her MIC studies. The selected antibiotics were shown to exhibit different activity levels in the presence of degradation products of ORC. Specifically, rifampin and gentamycin activity was impaired by degradation products of ORC and MIC was increased; clindamycin and tetracycline activity showed no change in the presence of ORC and no change in MIC. However, surprisingly, only minocycline MIC was reduced when mixed with degradation products of ORC.

In the tertiary stage, degradation products of ORC pads impregnated with selected antibiotics including minocycline, rifampin and/or clindamycin were used. MIC results were found to be consistent with those of the secondary stage.

The levels of clindamycin required to be impregnated onto the ORC pad in order to achieve an inhibition of growth with degradation products of ORC were similar to those of the first stage MIC, i.e. there was no change of clindamycin antimicrobial activity. The levels of rifampin required to be impregnated onto the ORC pad used for production of degradation products of ORC in order to achieve an inhibition of growth were about 50 times higher than those of the first stage MIC i.e. the rifampin activity was impaired even when impregnated onto the ORC pad. Finally, the levels of minocycline required to be impregnated onto the ORC pad in order to achieve an inhibitory effect were about 20 times lower than those of the first stage MIC.

It was further found that when minocycline is impregnated onto an ORC pad in combination with an additional antibiotic, the ET50 was reduced for both minocycline and the additional antibiotic, i.e. either rifampin or clindamycin. As little as 1.26 ng/ml minocycline, together with 366.5 ng/ml rifampin or 8.9 ng/rill clindamycin were found to be sufficient for growth inhibition of S. aureus. The MIC for these antibiotics when used as single antibiotics in the absence of ORC (first stage MIC results) was found to be 250 ng/ml for minocycline, 62 ng/ml for clindamycin and 15 ng/ml for rifampin. These results prove a 200-fold reduction of the MIC for minocycline, and 6.8-fold reduction for clindamycin. Although the MIC for rifampin was higher than that seen as a single antibiotic, it remained less than that of the second stage MIC. Interestingly, even though minocycline is an antibiotic from the tetracycline family of antibiotics, the activity enhancement was restricted to minocycline and was not demonstrated for other members of the family (tetracycline).

The results demonstrate a synergistic effect for minocycline and degradation products of ORC. Degradation products obtained from a hemostatic ORC pad impregnated with a low concentration of minocycline are therefore able to provide a high level of antibiotic activity. The recommended antibiotic concentration for minocycline alone in an ORC pad is in the range of from 2.7 µg to 21.6 µg per gram ORC. When minocycline is used in combination with rifampin or clindamycin, the recommended antibiotic concentrations are from 0.5 µg to 2.7 µg minocycline per gram ORC together with from 31.4 µg to 157 µg rifampin per gram ORC or from 0.6 µg to 3.8 µg clindamycin per gram ORC.

The invention claimed is:

1. A method for the treatment of an infection in a subject in need thereof, the method comprising administering to the subject an antimicrobial composition comprising an extract of at least one degradation product of an oxidized regenerated cellulose (ORC) substrate in a solid form, and an antibiotic being minocycline, wherein the at least one degradation product comprises one or more members selected from the group consisting of a monosaccharide and an oligosaccharide, and wherein the carboxyl content of the ORC is about 12% to about 21%, by weight.

2. The method of claim 1, wherein the antimicrobial composition is devoid of an additional antibiotic.

3. The method of claim 1, wherein the minocycline is present in the antimicrobial composition at a concentration of from about 12.6 ng/ml.

4. The method of claim 1, wherein the antimicrobial composition further comprises at least one additional antibiotic.

5. The method of claim 1, wherein the substrate is in the form selected from the group consisting of a cloth, a pad, and a mesh, and wherein the minocycline is dispersed on and/or within the cloth, the pad, or the mesh.

* * * * *